United States Patent [19]

Penny et al.

[11] Patent Number: 5,315,018

[45] Date of Patent: May 24, 1994

[54] PROCESS FOR THE FUNCTIONALIZATION OF ORGANIC MOLECULES

[75] Inventors: Stuart J. Penny, Maltby; Roy H. Valentine, Guisborough, both of England

[73] Assignee: Roussel-Uclaf, Paris, France

[21] Appl. No.: 991,076

[22] Filed: Dec. 15, 1992

[30] Foreign Application Priority Data

Dec. 18, 1991 [GB] United Kingdom ............... 91-26876

[51] Int. Cl.$^5$ ........................................... C07D 317/54
[52] U.S. Cl. .................................. 549/445; 549/447; 549/434
[58] Field of Search ................... 549/447, 445, 434

[56] References Cited

U.S. PATENT DOCUMENTS 2,878,265 3/1959 Wachs et al. .

FOREIGN PATENT DOCUMENTS 632589 11/1949 United Kingdom .
839494 6/1960 United Kingdom .

*Primary Examiner*—Nicky Chan
*Attorney, Agent, or Firm*—Nixon & Vanderhye

[57] ABSTRACT

The present invention relates to the hydroxymethylation of aromatic compounds and the subsequent transformation of the hydroxymethylated aromatic compounds to the polyalkoxyalkylene derivative thereof.

6 Claims, No Drawings

PROCESS FOR THE FUNCTIONALIZATION OF ORGANIC MOLECULES

The present invention relates to the hydroxymethylation of aromatic compounds and the further transformation of the hydroxymethyl aromatic compounds so formed.

In one particular preferred embodiment the present invention relates to an improved method of preparing piperonyl butoxide in a cost effective manner removing the risk of liberating toxic bis-chloromethyl ether (BCME) as a noxious bi-product.

In another embodiment the present invention relates to a method of preparing compounds useful in perfumes or fragrances, e.g. Cumenal, piperonal, anisaldehyde, T Butyl benzaldehyde and chloromethyl naphthalene.

In a further embodiment the present invention relates to a method of preparing ion-exchange resins by chloromethylation.

Compounds such as piperonyl butoxide are representative of a class of compounds known as insecticidal synergists represented by the general formula (1):

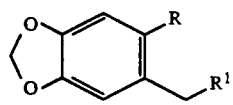
(1)

where R is hydrogen or C1-6 alkyl and R1 is a polyalkoxyalkylene type side chain such as butylcarbityl. (For piperonyl butoxide R=n-propyl and $R_1$=nBuO(CH$_2$.)$_2$O(CH$_2$)$_2$O—).

The preparation of such compounds has been extensively described in the literature (see for example U.S. Pat. No. 2,485,680 and British Patent 632589). The process to such compounds (exemplified by piperonyl butoxide) is generally carried out by reaction of a halide such as (2) with the sodium salt of a polyalkoxymethylene alcohol (3).

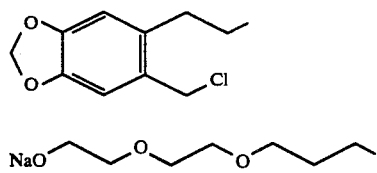
(2)

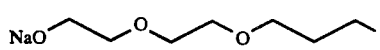
(3)

The halides of formula (2) can be readily prepared by reaction of formaldehyde and hydrochloric acid on dihydrosafrole (4).

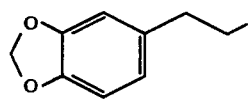
(4)

Alternatively compounds such as (1) may be prepared by reacting sodium salts of benzyl alcohols such as (5) with butylcarbityl halides such as (6). (British Patent 632 589).

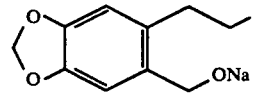
(5)

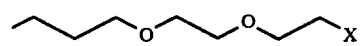
(6)

X = Cl, Br

The benzyl alcohol required for (5) can be prepared by converting halide (2) into its acetate and then saponifying the ester.

Both of the above routes proceed via chloromethylation of dihydrosafrole (4) with formaldehyde and hydrochloric acid. It is well known in the literature that bis-chloromethyl ether (BCME) is formed when hydrogen chloride (or hydrochloric acid) and formaldehyde are mixed. (L. S. Frankel et al., Environmental Science & Technology 1974, 8, (4), 356). BCME is a powerful respiratory carcinogen. (FJC Roe, The Lancet, 1985, 268; J. L. Gargus et al., Toxicology & Applied Pharmacology 1969, 15, 92; B. L. Van Duuren et al., J.Nat.Cancer,Inst., 1969, 43, 481; Chem.Eng.News, 1972, 50 (13) 55; Org.Reactions, 1972 (19), 422 and Amer.Indust.Hygiene Assoc.J. 1972, 381). The current occupational exposure limit for BCME is 0.001 ppm (0.005 mg m-3) which is one of lowest limits quoted. The elimination of the possibility of the formation of BCME from a process to make synergists and related compounds such as piperonyl butoxide provides an important advantage over current known routes.

Refinements to existing processes have been claimed (U.S. Pat. No. 2,878,265) but chloromethylation chemistry is still central to prepare compounds such as (1). Thus British Patent 839,494 describes an improved way of making chloromethyl dihydrosafrole and highlights a problem which often occurs in this chloromethylation chemistry, the formation of diphenylmethane "dimer" (7).

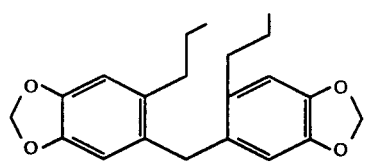
(7)

The improvement in British Patent 839 494 consists of the virtual elimination of formation of (7) and other polymeric products. However the process still uses formaldehyde and hydrochloric acid.

The Lederer-Manasse reaction allows for the condensation of an aromatic phenol or ether with formaldehyde to yield a benzyl alcohol. (Scheme 1)

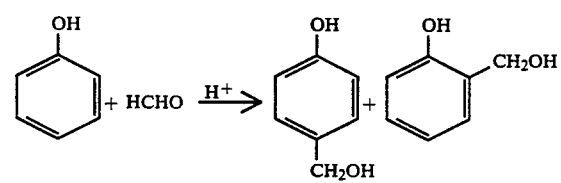

Scheme 1

Attempts to carry out this reaction on dihydrosafrole (4) result in formation of high yields of "dimer" (7) with a wide range of acid catalysts including trifluoroacetic acid, phosphoric acid, formic acid, p-toluenesulphonic acid, sulphuric acid at a range of concentrations.

It has now been discovered that the hydroxymethylation of activated aromatic molecules may be carried out to give a protected derivative, the protecting group then being cleaved to give the hydroxymethyl compound without substantial bi-product formation. Thus compounds such as (1), for example piperonyl butoxide, can be prepared by a route which avoids the possible formation of BCME, minimises the formation of "dimer" (2) and thus allows for a safer and more attractive industrial process.

Accordingly, the present invention provides a process for the hydroxymethylation of an activated aromatic molecule which comprises the reaction of the activated aromatic molecule with formaldehyde in a carboxylic acid in the presence of an acid catalyst. The carboxylic acid is preferably a $C_{2-10}$ carboxylic acid, for example acetic, benzoic or naphthoic acid. The acid catalyst preferably does not contain chloro or bromo atoms is conveniently a dilute mineral acid, e.g. dilute sulphuric acid, a dilute sulphonic acid, trifluoroacetic acid or a Lewis acid such as boron trifluoride, preferably dilute sulphuric acid. The carboxylic acid may be in the form of a protected acid derivative such as an anhydride, for example acetic anhydride or a mixed anhydride. The reaction is normally carried out at a non-extreme temperature, for example between 20° and 100° C. suitably between 20° and 90° C. and preferably between 60° and 90° C. The reaction may also be carried out under sealed conditions, for example in an autoclave, in which case the reaction may be carried out at a higher temperature, for example between 100° and 150° C. A water immiscible organic solvent may also be added to the reaction to give a multiphase system; $C_{5-10}$ alkanes or cycloalkanes for example hexane is a suitable immiscible organic solvent for use in the reaction. This reaction provides the hydroxymethylated aromatic molecule in the form of an esterified derivative, the free hydroxyl group may be generated by cleavage of the ester group under conventional conditions, for example aqueous sodium hydroxide solution. Suitable activating groups for the aromatic molecule include ($C_1$–$C_6$) alkyl, ($C_1$–$C_6$) alkoxy and $C_{1-6}$ polyalkoxy groups.

The activated aromatic molecule may be a heterocyclic polycarbocyclic, polyheterocyclic molecule or phenyl substituted by a suitable activating group. Polyaromatic rings conveniently contain up to five and preferably two or three rings. Heterocyclic molecules conveniently contain a maximum of five and preferably one to three hetero atoms chosen from nitrogen, oxygen and sulphur.

By formaldehyde is meant the use of aqueous formaldehyde or preferably a solid formaldehyde polymer such as paraformaldehyde which acts as a formaldehyde precursor. Paraformaldehyde is a particularly convenient form for use in this invention.

Thus, the reaction of dihydrosafrole (4) with formaldehyde in acetic acid in the presence of catalytic amounts of an acid at a non extreme temperature, for example between 40° C.–100° C., preferably 60°–80° C., gives acetate (8) in substantial amounts.

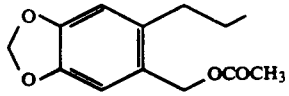

(8)

It has also been discovered that yields of the desired intermediate (8) can be improved by conducting the reaction in a multi-phase system. Thus dihydrosafrole (4) is reacted with formaldehyde in acetic acid in the presence of a catalytic amount of sulphuric acid with the addition of an immiscible non-reactive solvent, conveniently a hydrocarbon such as hexane to give (8) in nearly 60% yield.

By an immiscible hydrocarbon solvent, the invention includes any liquid alkane, cycloalkane or other saturated hydrocarbon. Convenient solvents include pentanes, kerosenes and similar aliphatic petroleum distillates, as well as cyclohexane. Preferably hexane is used.

The hydroxymethyl compound, or its esterified derivative may be converted to the corresponding halomethyl aromatic molecule by conventional means. Thus, in a second aspect the present invention provides a process for the halomethylation of an activated aromatic molecule which process comprises:

(i) the hydroxymethylation of the activated aromatic molecule by reaction of the activated aromatic molecule with formaldehyde in a carboxylic acid in the presence of an acid catalyst and, thereafter, optionally cleaving the acyl group, and (ii) halogenating the product from (i) to give the corresponding halomethylated aromatic molecule. Suitably the halogenation is chlorination. Suitable halogenating agents are well known to those skilled in the art and include thionyl chloride, phosphorous oxychloride, phosphorous pentachloride, oxalyl chloride. The reaction is conveniently carried out at a non-extreme temperature, i.e. between −20° and 80° C., preferably 20°–30° C.

Thus, acetate (8) can be reacted with thionyl chloride at a temperature from about 0° C. up to 50° C. and preferably at ambient temperature (20°–30° C.) to give chloromethyldihydrosafrole (2).

The chloromethyl intermediate (2) may then be converted to piperonyl butoxide using chemistry well known in the literature.

Alternatively the hydroxymethyl compound or its esterified derivative may be oxidised to give the corresponding aldehyde. This is a convenient method of inserting an aldehyde function on a polyaromatic or heteroaromatic ring. The following examples are provided to illustrate the invention:

EXAMPLE 1

Preparation of 4,5-methylenedioxy-2-propylbenzyl acetate

A mixture of dihydrosafrole, 25 g, in acetic acid (25 g) was added, with stirring over 3 hours to a mixture of acetic acid (230 g), paraformaldehyde (45 g) and sulphuric acid (10%, 1.6 g) held at 70° C. After the reaction had been shown to be complete by glc, the excess paraformaldehyde was removed by filtration and the filtrate poured into water (450 ml). Sodium hydroxide solution (20 ml of a 10% solution) was then added. Ether extraction, followed by drying over magnesium sulphate, filtration and evaporation of solvent gave an oil. Methanol (30 ml) was added and after cooling to 0°

C. a colourless precipitate of "dimer" (7) was removed by filtration. Evaporation of the filtrate gave 12.7 g of an oil which was purified by distillation to give 7.3 g of colourless oil as 4,5-methylenedioxy-2-propylbenzyl acetate. (b.p. 176°–185° C. at 0.4 mmHg).

EXAMPLE 2

Preparation of 4,5-methylenedioxy-2-propylbenzyl chloride (2), (chloromethyldihydrosafrole)

Thionyl chloride (1.5 g) was added in one portion to a stirred solution of 4,5-methylenedioxy-2-propylbenzyl acetate (1.5 g) in dichloromethane (20 ml). After stirring for 2 hours the reaction appeared to have proceeded to completion by glc. The mixture was then poured into water and the organic layer separated and dried over magnesium sulphate. Removal of dichloromethane after filtration gave 4,5-methylene-dioxy-2-propylbenzyl chloride (2), (1.1 g) as a colourless oil.

Analysed by glc: SE30 packed column at 125° C. temperature programmed to 200° C.

EXAMPLE 3

Preparation of piperonyl butoxide

A reaction mixture of 4,5-methylenedioxy-2-propylbenzyl chloride (2) (1.0 g), and the potassium salt of butyl carbitol (2.0 g) in petroleum ether (25 ml) was heated at 80° C. for 2 hours. A further aliquot of the potassium salt of butyl carbitol was added (2.0 g) and heating continued for a further hour. The mixture was then poured into water. Separation of the organic phase, followed by drying and evaporation gave piperonyl butoxide (2.8 g) as a clear yellow oil.

Analysed by glc: SC30 packed column gave a single peak with identical retention time to authentic piperonyl butoxide.

EXAMPLE 4

Preparation of 4,5-methylenendioxy-2-propylbenzyl acetate (8)

Dihydrosafrole (20 g), acetic acid (100 g) and water (10 g) were added to a mixture of acetic acid (250 ml), hexane (200 ml), acetic anhydride (40 g) and paraformaldehyde (40 g) to which 1.7 g of 40% sulphuric acid had been added. The reaction mixture was held at 60° C. for 5 hours and was then cooled to 20° C. and excess paraformaldehyde removed by filtration. Saturated brine (200 ml) was then added followed by ether (100 ml). The mixture was ether extracted (3 times) and combined extracts washed with brine (3 times). Following removal of solvent under reduced pressure the material was distilled under vacuum to give 4,5-methylene-dioxy-2-propylbenzyl acetate (8) as a colourless oil (b.pt 154°–165° C. at 2.0 mm Hg) . . . Yield 59%.

We claim:

1. A process for the preparation of a compound of the formula:

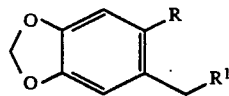

wherein R is a hydrogen atom or a $C_1$-$C_6$-alkyl group, and $R^1$ is a polyalkoxyalkylene group, which comprises (a) reacting a compound of the formula:

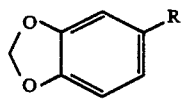

with formaldehyde in a carboxylic acid of the formula:

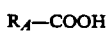

wherein $R_A$ is a $C_1$-$C_9$ hydrocarbyl group or a protected derivative thereof in the presence of an acid catalyst to produce an esterified hydroxymethylated derivative of the formula:

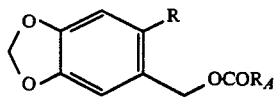

which is thereafter (b) halogenated to produce a compound of the formula:

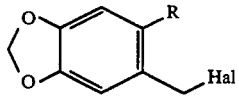

wherein Hal is an halogen atom,
and thereafter (c) reacting the halogenated compound with HO—$R^1$ or the sodium salt thereof to produce a compound of formula I.

2. The process as claimed in claim 1 wherein $R_A$-COOH is in the form of an anhydride.

3. The process as claimed in claim 1 or claim 2 wherein a water immiscible organic solvent is added to the reaction mixture of step (a).

4. The process as claimed in claim 1 wherein R is a linear propyl group and $R^1$ is n—BuO(CH$_2$)$_2$O(CH$_2$)$_2$O—.

5. The process as claimed in claim 2 wherein R is a linear propyl group and $R^1$ is n—BuO(CH$_2$)$_2$O(CH$_2$)$_2$O—.

6. The process as claimed in claim 3 wherein R is a linear propyl group and $R^1$ is n—BuO(CH$_2$)$_2$O(CH$_2$)$_2$O—.

* * * * *